US005650396A

United States Patent [19]
Carlino et al.

[11] Patent Number: 5,650,396
[45] Date of Patent: Jul. 22, 1997

[54] METHODS OF MODULATING INFLAMMATORY CYTOKINES IN THE CNS USING TGF-β

[75] Inventors: Joseph A. Carlino, San Leandro, Calif.; Etty N. Benveniste, Birmingham, Ala.

[73] Assignee: Celtrix Pharmaceuticals, Inc., Santa Clara, Calif.

[21] Appl. No.: 213,001

[22] Filed: Mar. 15, 1994

[51] Int. Cl.$^6$ .................................................. A61K 38/00
[52] U.S. Cl. ................................................................ 514/21
[58] Field of Search ................................................ 514/21

[56] References Cited

PUBLICATIONS

Beutler et al., "The biology of cachectin/TNF–A primary mediator of the host response" Ann. Rev. Immunol. (1989) 7:625–655.
Selmaj et al., "Tumor necrosis factor mediates myelin and oligodendrocyte damage in vitro" Ann. Neurol. Assoc. (1988) 23:339–346.
Robbins et al., "Production of cytotoxic factor for oligodendrocytes by stimulated astrocytes" J. Immunol. (1987) 139:2593–2597.
Raine, "Biology of disease: Analysis of autoimmune demyelination: Its impact upon multiple sclerosis" Lab. Invest. (1984) 50:608–635.
Selmaj, "Proliferation of astrocytes in vitro in response to cytokines. A primary role for tumor necrosis factor" J. Immunol. (1990) 144:129–135.
Panek et al., "Tumor necrosis factor α response elements in the HLA–DRA promoter: Identification of a tumor necrosis factor α–induced DNA–protein complex in astrocytes" Proc. Natl. Acad. Sci. USA (1992) 89:11518–11522.
Benveniste, "Inflammatory cytokines within the central nervous systems: sources, function, and mechanism of action" Am. J. Physiol.: Cell Physiol. (1992) 263:32:C1–C16.
Hofman, "Tumor necrosis factor identified in multiple sclerosis brain" J. Exp. Med. (1989) 170:607–612.
Selmaj, "Identification of lymphotoxin and tumor necrosis factor in multiple sclerosis lesions" J. Clin. Invest. (1991) 87:949–954.
Sharief et al., "Association between tumor necrosis factor–α and disease progression in patients with multiple sclerosis" N. Eng. J. Med. (1991) 325:467–472.
Sharief et al., "Increased levels of circulating ICAM–1 in serum and cerebrospinal fluid of patients with active multiple sclerosis. Correlation with TNF–α and blood–brain barrier damage" J. Neuroimmunol. (1993) 43:15–21.
Ruddle et al., "An antibody to lymphotoxin and tumor necrosis factor prevents transfer to experimental allergic encephalomyelitis" J. Exp. Med. (1990) 172:1193–1200.
Selmaj et al., "Anti–tumor necrosis factor therapy abrogates autoimmune demyelination" Ann. Neurol. (1991) 30:694–700.
Chung et al., "Tumor necrosis factor–α production by astrocytes: Induction by lipopolysaccharide, IFN–γ and IL–1β" J. Immunol. (1990) 144:2999–3007.

Lieberman et al., "Production of tumor necrosis factor and other cytokines by astrocytes stimulated with lipopolysaccharide or a neurotropic virus" Proc. Natl. Acad. Sci. USA (1989) 86:6348–6352.
Chung et al., "Role of protein kinase C activity in tumor necrosis factor–α gene expression: Involvement at the transcriptional level" J. Immunol. (1992) 149:3894–3902.
Lieberman et al., "Protein kinase regulates tumor necrosis factor mRNA stability in virus–stimulated astrocytes" J. Exp. Med. (1990) 172:989–992.
Lieberman et al., "Poly(A) removal is the kinase–regulated step in tumor necrosis factor mRNA decay" J. Biol. Chem. (1992) 267:2123–2126.
Benveniste et al., "Intracellular second messengers involved in both induction and inhibition of TNF–α expression by astrocytes" J. Immunol. (1993) 150:245A.
Fisher et al., "Role of tyrosine kinase signalling in newcastle disease virus (NDV) mediated TNF–α gene activation in astrocytes" J. Immunol. (1993) 150:295A.
Frei et al., "On the cellular source and function of interleukin 6 produced in the central nervous system in viral diseases" Eur. J. Immunol. (1993) 19:689–694.
Norris et al., "Interleukin–6 production by astrocytes: Induction by the neurotransmitter norepinephrine". J. Neuroimmunol. (1993) 45:137–146.
Norris et al., "Signal transduction pathways mediating astrocyte IL–6 induction by IL–1β and tumor necrosis factor–α" J. Immunol. (1994) 152:841–850.
Hirano et al., "Biological and clinical aspects of interleukin 6" Immunology Today (1990) 11:443–449.
Aderka et al., "IL–6 inhibits lipopolysaccharide–induced tumor necrosis factor production in cultured human monocytes, U937 cells, and in mice" J. Immunol. (1989) 143:3517–3523.
Merrill, "Proinflammatory and antiinflammatory cytokines in multiple sclerosis and central nervous system acquired immunodeficiency syndrome" J. Immunother. (1992) 12:167–170.
Massagué, "The transforming growth factor–β family" Annu. Rev. Cell. Biol. (1990) 6:597–641.
da Cunha et al., "Glial cell–specific mechanisms of TGF–β1 induction by IL–1 in cerebral cortex" J. Neuroimmunol. (1993) 42:71–86.
Morganti–Kossmann et al., "Autocrine and paracrine regulation of astrocyte function by transforming growth factor–β" J. Neuroimmunol. (1992) 39:163–174.

(List continued on next page.)

Primary Examiner—Paul J. Killos
Attorney, Agent, or Firm—Morrison & Foerster

[57] ABSTRACT

Methods for modulating the expression of inflammatory cytokines in the central nervous system comprising administering an effective amount of TGF-β are disclosed. The methods include suppressing pro-inflammatory cytokines in the central nervous system by administering an effective amount of TGF-β and inducing anti-inflammatory cytokines in the central nervous system by administering an effective amount of TGF-β.

3 Claims, 14 Drawing Sheets

OTHER PUBLICATIONS

Suzumura et al., "Transforming growth factor–β suppresses activation and proliferation of microglia in vitro" *J. Immunol.* (1993) 151:2150–2158.

Schluesener, "Transforming growth factors type β1 and β2 suppress rat astrocyte autoantigen presentation and antagonize hyperinduction of class II major histocompatibility complex antigen expression by interferon–γ and tumor necrosis factor–α" *J. Neuroimmunol.* (1990) 27:41–47.

Lindholm et al., "Transforming growth factor–β1 in the rat brain: increase after injury and inhibition of astrocyte proliferation" *J. Cell Biol.* (1992) 117:395–400.

Barnum et al., "Transforming growth factor–β1 inhibits inflammatory cytokine–induced C3 gene expression in astrocytes" *J. Immunol.* (1994) 152:765–773.

Miller, "Suppressor T cells generated by oral tolerization to myelin basic protein suppress both in vitro and in vivo immune responses by the release of transforming growth factor β after antigen–specific triggering" *Proc. Natl. Acad. Sci. USA* (1992) 89:421–425.

Johns et al., "Successful treatment of experimental allergic encephalomyelitis with transforming growth factor–β1" *J. Immunol.* (1991) 147:1792–1796.

Kuruvilla, "Protective effect of transforming growth factor $β_1$ on experimental autoimmune diseases in mice" *Proc. Natl. Acad. Sci. USA* (1991) 88:2918–2921.

Racke et al., "Prevention and treatment of chronic relapsing experimental allergic encephalomyelitis by transforming growth factor–β1" *J. Immunol.* (1991) 146:3012–3017.

Khoury et al., "Oral tolerance to myelin basic protein and natural recovery from experimental autoimmune encephalo–myelitis are associated with downregulation of inflammatory cytokines and differential upregulation of transforming growth factor β, interleukin 4, and prostaglandin E expression in the brain" *J. Exp. Med.* (1992) 176:1355–1364.

Santambrogio et al., "Studies on the mechanisms by which transforming growth factor–β (TGF–β) protects against allergic encephalomyelitis: Antagonism between TGF–β and tumor necrosis factor" *J. Immunol.* (1993) 151:1116–1127.

Nesbitt et al., "Differential regulation of interleukin–6 receptor and gp130 gene expression in rat hepatocytes" *Mol. Biol. of the Cell* (1992) 3:103–112.

Bogdan et al., "Contrasting mechanisms for suppression of macrophage cytokine release by transforming growth factor–β and interleukin–10". *J. Biol. Chem.* (1992) 267:23301–23308.

Dubois et al., "Transforming growth factor β is a potent inhibitor of interleukin 1 (IL–1) receptor expression: Proposed mechanism of inhibition of IL–1 action" *J. Exp. Med.* (1990) 172:737–744.

Pinson et al., "Regulation by transforming growth factor–β1 of expression and function of the receptor for IFN–γ on mouse macrophages" *J. Immunol.* (1992) 149:2028–2034.

McGee et al., "Transforming growth factor–β and IL–1β act in synergy to enhance IL–6 secretion by the intestinal epithelial cell line, IEC–6" *J. Immunol.* (1993) 151:970–978.

Elias et al., "Transforming growth factor–β regulation of IL–6 production by unstimulated and IL–1 stimulated human fibroblasts" *J. Immunol.* (1991) 146:3437–3443.

Tanabe et al., "Genomic structure of the murine IL–6 gene: High degree conservation of potential regulatory sequences between mouse and human" *J. Immunol.* (1988) 141:3875–3881.

Isshiki et al., "Constitutive and interleukin (IL–1)–inducible factors interact with the IL–1–responsive element in the IL–6 gene" *Mol. Cell. Biol.* (1990) 10:2757–2764.

Akira et al., "Regulation of expression of the interleukin 6 gene: Structure and function of the transcription factor NF–IL6" *Ciba Foundation Symposium* 167, A Wiley–Interscience Publication (1992) pp. 47–67.

Sparacio et al., "Cytokine regulation of interleukin–6 gene expression in astrocytes involves activation of an NK–κB–like nuclear protein" *J. Neuroimmunol.* (1992) 39:231–242.

Kim et al., "Autoinduction of transforming growth factor β1 is mediated by the AP–1 complex" *Mol. Cell. Biol.* (1990) 10:1492–1497.

Rossi et al., "A nuclear factor 1 binding site mediates the transcriptional activation of a type 1 collagen promoter by transforming growth factor–β" *Cell* (1988) 52:405–414.

Riccio et al., "Transforming growth factor β1–responsive element: Closely associated binding sites for USF and CCAAT–binding transcription factor–nuclear factor I in the type 1 plasminogen activator inhibitor gene" *Mol. Cell. Biol.* (1992) 12:1846–1855.

Lin et al., "Regulation of transcription of the germ–line Igα constant region gene by an ATF element and by novel transforming growth factor–β1–responsive elements" *J. Immunol.* (1992) 149:2914–2925.

Loughlin et al., "Regulation of Fc receptor and major histocompatibility complex antigen expression on isolated rat microglia by tumour necrosis factor, interleukin–1 and lipopolysaccharide: effect on interferon–gamma induced activation" *Immunology* (1992) 75:170–175.

Baker et al., "Cytokines in the central nervous system of mice during chronic relapsing experimental allergic encephalomyelitis" *Cell. Immunol.* (1991) 134:505–510.

Wahl et al., "Macrophage– and astrocyte–derived transforming growth factor β as a mediator of central nervous system dysfunction in acquired immune deficiency syndrome" *J. Exp. Med.* (1991) 173:981–991.

CA 119: 218309 1993.

CA 119: 196575 1993.

Medline 94312763 Mar. 1994.

METHODS OF MODULATING INFLAMMATORY CYTOKINES IN THE CNS USING TGF-β

FIELD OF INVENTION

This invention relates to methods of modulating inflammatory cytokines in the central nervous system (CNS) by administering an effective amount of TGF-β. Methods of suppressing pro-inflammatory cytokines and of inducing anti-inflammatory cytokines in the CNS by administering TGFβ are within the scope of the present invention.

This work was supported by Grants RG-2269-A4 and RG-2205-B5 (E.N.B.) from the National Multiple Sclerosis Society, and grants AI27290 and MH50421 (E.N.B.) from the National Institutes of Health.

BACKGROUND ART

TNF-α is a 17 kDa peptide produced by a wide variety of cells during host response to microbial infections and neoplastic diseases (for review see (1)). TNF-α is recognized to be an important mediator of inflammatory responses in a variety of tissues, including the brain, and may play an important role in the initiation of inflammation and the pathologic consequences that result from this process. TNF-α has a diverse range of functions in the central nervous system (CNS) because of its effects on oligodendrocytes and astrocytes. Most relevant to CNS disease is the ability of TNF-α to mediate myelin and oligodendrocyte damage in vitro (2), and its ability to cause cell death of oligodendrocytes in vitro (3). This aspect of TNF-α activity may contribute directly to myelin damage and/or the demyelination process observed in diseases such as multiple sclerosis (MS) and experimental allergic encephalomyelitis (EAE). TNF-α has multiple effects on the astrocyte which are noncytotoxic in nature. One of the pathologic features of demyelinated plaques in MS is astrogliosis, in which proliferation of astrocytes and production of glial fibrillary acidic protein (GFAP) occurs (4). Astrocyte proliferation leads to the reactive gliosis associated with MS, and TNF-α contributes to this process (5). TNF-α alone has no effect on class II major histocompatibility complex (MHC) expression by astrocytes, but acts to enhance expression initially stimulated by IFN-γ by increasing IFN-γ-induced transcription of the class II gene (6). TNF-α is also a potent inducer of cytokine production by astrocytes, inducing the colony-stimulating factors M-CSF, G-CSF and GM-CSF, IL-6, and TNF-α itself (for review see (7)).

In vivo studies of murine, rat and human demyelinating diseases indicate that TNF-α participates in the inflammatory reactions that take place within the CNS. TNF-α positive astrocytes and macrophages have been identified in the brains of MS patients, particularly in the plaque region (8). Selmaj et al. (9) have determined that both TNF-α and TNF-β are present in MS plaque regions, and that TNF-α is localized within astrocytes whereas TNF-β is associated with microglia and T-cells. Increased serum and cerebrospinal fluid levels of TNF-α have been documented in patients with MS (10), and a strong correlation exists between cerebrospinal fluid levels of TNF-α, disruption of the blood brain barrier, and high levels of circulating ICAM-1 in patients with active MS (11). These findings indicate that TNF-α is present in active demyelinated plaques, and TNF-α levels in the cerebrospinal fluid of MS patients correlate with disease progression. In EAE, several studies have demonstrated that antibody to TNF-α/TNF-β could prevent the transfer of EAE by encephalitogenic T-cells (12, 13). Preincubation of myelin basic protein (MPB)-sensitized T-cells with anti-TNF antibody in vitro prior to injection did not diminish their ability to transfer EAE, suggesting that anti-TNF antibody inhibits EAE development by interfering with the effector phase of the disease (13).

Astrocytes, the most abundant glial cells in the CNS, produce TNF-α in response to a variety of stimuli, including LPS, the cytokines IL-1β and IFN-γ, and Newcastle's disease virus (NDV) (14, 15). Activation of protein kinase C (PKC). by IFN-γ, IL-1β and NDV is necessary for subsequent induction of TNF-α gene expression by primary rat astrocytes (16, 17). PKC activity appears to be required for both transcription of the TNF-α gene (16) as well as TNF-α mRNA stability (17, 18). In addition, more recent data demonstrates that not only is PKC activity required for astrocyte TNF-α expression, but tyrosine kinase (TK) activity is also needed (19, 20).

Astrocytes produce another cytokine, IL-6, in response to a variety of stimuli including IL-1, TNF-α, PMA, cAMP agonists, norepinephrine and virus (15, 21, 22, 23). IL-6 is also implicated in contributing to CNS inflammation and immune responsiveness due to its ability to promote astrogliosis, immunoglobulin production, and T-cell activation (5, 24). Interestingly, IL-6 has also been suggested to act as an anti-inflammatory cytokine due to its ability to down-regulate TNF-α expression (25). Also, IL-6 has been found at the lesion edge of burnt-out plaques in MS brain, rather than in active plaques (26), suggesting it may be involved in resolution of disease.

TGF-β is a protein of ~28 kDA that is synthesized by many cell types (for review see (27)). Within the CNS, astrocytes, microglia and oligodendrocytes are capable of producing TGF-β upon activation (28, 29). The actions of TGF-β are pleiotropic and include inhibiting the proliferation of many cell types, promoting the growth of new blood vessels, and inhibiting some immune and inflammatory responses. TGF-β can modulate the activity of glial cells by inhibiting IFN-γ-induced class II MHC expression on astrocytes and microglia (30, 31), inhibiting proliferation of astrocytes and microglia (30, 32), and inhibiting cytokine-induced C3 gene expression in astrocytes (33). Of relevance to demyelinating diseases, CD4+ and CD8+T cells that regulate recovery from EAE produce TGF-β (34, 35), and TGF-β is capable of inhibiting IFN-γ and TNF-α production by the CD4+ effector T-cells that transfer disease (34, 36). Additionally, these data correlate well with the in vivo studies demonstrating that injection of TGF-β improves the clinical course of EAE (37, 38, 39), injection of anti-TGF-β antibodies results in an increase in severity and duration of disease (35), and expression of TGF-β is detected in the CNS of animals in recovery (40). A recent study by Santambrogio et al. (41) examined the mechanism(s) by which TGF-β protects against EAE. The authors suggest that the protective effect of TGF-β is exerted at the level of the target organ (the CNS), and that TGF-β may act by inhibiting both the production TNF-α and its effects within the CNS in addition to its effects on the vasculature.

DETAILED DESCRIPTION OF THE INVENTION

The invention is based on the discovery that TGF-β alone has no effect on TNF-α expression, but acts in a dose- and time-dependent manner to inhibit TNF-α mRNA and protein expression. Inhibition of TNF-α mRNA steady-state levels by TGF-β is not due to an effect on TNF-α mRNA stability, but rather to inhibition of TNF-α gene transcription. In contrast, TGF-β induces expression of IL-6 by astrocytes, and acts in a synergistic fashion with IL-1β or TNF-α for enhanced IL-6 expression. This effect of TGF-β is mediated by transcriptional activation of the IL-6 gene. Thus, TGF-β can differentially affect TNF-α and IL-6 production by astrocytes within the CNS.

We have discovered that transforming growth factor-β (TGF-β) inhibits TNF-α expression, and induces/enhances IL-6 expression by primary rat astrocytes. Treatment of astrocytes with TGF-β alone has no effect on TNF-α mRNA or protein expression; however, TGF-β suppressed induction of TNF-α expression by three different stimuli (IFN-γ/LPS, IFN-γ/IL-1β, TNF-α) at both the protein and mRNA level. The extent of TGF-β-mediated inhibition was greatest when astrocytes were pretreated with TGF-β for 6–24 hour and then exposed to the inducing stimuli. Inhibition of TNF-α mRNA steady-state levels by TNF-β was due to inhibition of TNF-α gene transcription, rather than degradation of the TNF-α message. In contrast, TGF-β alone induced expression of IL-6 by astrocytes, and synergized with two other cytokines, IL-1β and TNF-α, for enhanced IL-6 expression. TGF-β-induced/enhanced IL-6 expression was mediated by transcriptional activation of the IL-6 gene. These results demonstrate that TGF-β is an important regulator of cytokine production by astrocytes under inflammatory conditions in the brain.

We have also discovered that TGF-β exerts a contrasting effect on cytokine production by astrocytes, inhibiting TNF-α expression and inducing/enhancing IL-6 expression. The features of TGF-β-mediated inhibition of TNF-α expression include 1) a time-dependency of inhibition; i.e., pretreatment with TGF-β results in optimal inhibition; 2) inhibition of both TNF-α protein and mRNA level by inhibition of TNF-α gene transcription; and 3) inhibition of TNF-α expression induced by three different stimuli: IFN-γ/LPS, IFN-γ/IL-1β and TNF-α.

TGF-β inhibits TNF-α expression in various cell types, but exerts its inhibitory effect on different levels of TNF-α gene expression depending on the cell type under study. For example, TGF-β inhibited LPS-induced TNF-α protein expression in primary murine macrophages by inhibiting translation of TNF-α mRNA, while having no effect on TNF-α mRNA steady-state levels or TNF-α gene transcription (43). We have demonstrated that in astrocytes, TGF-β inhibits both TNF-α protein and mRNA expression. TGF-β suppresses TNF-α mRNA steady-state levels in the astrocyte by inhibiting transcription of the TNF-α gene (FIG. 5), rather than promoting degradation of TNF-α mRNA (FIG. 4). Thus, in macrophages, TGF-β primarily inhibits translation of TNF-α mRNA, while in astrocytes the effect of TGF-β is predominantly at the transcriptional level. Another striking difference between these two cell types is the kinetics of TGF-β-mediated inhibition. In the astrocyte, moderate inhibition of TNF-α expression was observed when TGF-β was added simultaneously with the inducing stimuli (IFN-γ/LPS, IFN-γ/IL-1β, TNF-α), while pretreatment with TGF-β (6–24 hours), then exposure to the stimuli, lead to >85% inhibition of TNF-α mRNA and protein expression. This is in contrast to macrophages, where TGF-β inhibits TNF-α protein expression when added considerably later than the inducing stimulus of LPS (43). Additionally, TGF-β inhibits LPS-induced TNF-α expression in microglia when added simultaneously with LPS (30). These findings demonstrate that TGF-β-mediated inhibition of TNF-α expression in astrocytes and cells of the monocyte/macrophage lineage occurs under different conditions and by different mechanisms.

Inhibition of TNF-α transcription upon exposure to TGF-β in astrocytes results from a number of cellular modifications, including alterations in the number and/or affinity of the inducing stimuli receptors (IFN-γ, IL-1β, TNF-α, LPS). TGF-β inhibits the ability of IL-1 to induce IL-2 production by EL-46.1 cells by inhibiting IL-1 receptor expression (44), and inhibits IFN-γ-mediated macrophage activation by decreasing IFN-γ receptor expression (45). Thus, there is precedence for TGF-β to mediate its suppressive effects by modulating relevant receptor expression. Our data suggests, however, that this is not the case for TGF-β and astrocytes. As described in the Results section, TGF-β can enhance the ability of IL-1β and TNF-α to induce IL-6 (Table II). In experiments where astrocytes are pretreated with TGF-β for 3, 6 or 12 hours, then exposed to either IL-1β, IL-1β plus IFN-γ, or TNF-α, enhanced IL-6 production is comparable to that seen when TGF-β is added simultaneously with the inducing stimuli (data not shown). These results demonstrate that TGF-β pretreatment does not downregulate receptors for IL-1β, IFN-γ or TNF-α.

TABLE II

TGF-β Induces and Enhances IL-6 Production by Astrocytes

| Cell Treatment | | IL-6 Activity[a] (U/ml/1 × 10⁶ cells) | Fold Increase[i] |
|---|---|---|---|
| Control[b] | | 170 ± 20[h] | |
| TGF-β (ng/ml)[c] | 0.1 | 220 ± 78 | 0 |
| | 1.0 | 620 ± 142 | 2.3 |
| | 10.0 | 1,426 ± 221 | 5.3 |
| IL-1β[d] | | 3,720 ± 425 | 13.8 |
| IL-1β + TGF-β[e] | 0.1 | 4,868 ± 375 | 18.0 |
| | 1.0 | 12,240 ± 674 | 45.3 |
| | 10.0 | 34,200 ± 2,202 | 126.6 |
| TNF-α[f] | | 990 ± 120 | 3.7 |
| TNF-α + TGF-β[g] | 0.1 | 990 ± 120 | 3.7 |
| | 1.0 | 2,364 ± 435 | 8.7 |
| | 10.0 | 10,612 ± 667 | 39.3 |

[a]IL-6 activity assessed by B9 bioassay
[b]Culture medium alone for 18 h
[c]TGF-β₁, for 18 h
[d]IL-1β (1 ng/ml) for 18 h
[e]IL-1β (1 ng/ml) plus TGF-β for 18 h
[f]TNF-α (100 ng/ml) for 18 h
[g]TNF-α (100 ng/ml) plus TGF-β for 18 h
[h]Mean ± S.D. of two experiments
[i]Fold Increase is compared to control value With respect to astrocyte IL-6 production, we have shown that TGF-β alone induces both IL-6 mRNA and protein expression, and synergizes with the cytokines IL-1β or TNF-α for enhanced IL-6 expression. Comparable findings of a synergistic effect of TGF-β and IL-1 on IL-6 secretion by intestinal epithelial cells and lung fibroblasts has recently been reported (46, 47). Interestingly, in lung fibroblasts, TGF-β exerted a synergistic effect only with a sub-optimal concentration of IL-1, and actually inhibited IL-6 expression induced by optimal concentrations of IL-1. We have observed in the astrocyte that TGF-β synergizes with IL-1β at both sub-optimal and optimal IL-1β concentrations (0.01–1 ng/ml) (data not shown). TGF-β does not increase astrocyte IL-6 mRNA steady-state levels by stabilization of IL-6 message, but rather induces and enhances transcription of the IL-6 gene. The IL-6 promoter region contains numerous regulatory elements for transcription factors such as AP-1, CREB, NF-κB and NF-IL-6 (48, 49, 50). We have previously shown that IL-1β and TNF-α induction of IL-6 gene expression is transcriptionally regulated, and mediated, in part, via activation of NF-κB (51). TGF-β transcriptionally regulates a number of genes. TGF-β autoinduction is mediated by the AP-1 complex (52); TGF-β inducibility of the type I collagen promoter requires a CTF/NF-1 binding site (53); TGF-β induction of the type I plasminogen activator inhibitor gene utilizes both a CTF/NF-1 binding site and USF binding site (54); and the Igα constant region gene is induced by TGF-β via a novel TGF-β-response element (TGF-β-RE) (55). The IL-6 gene does not contain a USF binding site of TGF-β-RE, but does have binding sites for AP-1 and CTF/NF-1. Thus, it is possible that TGF-β may induce and/or enhance expression of the IL-6 gene through induction of AP-1 and/or CTF-NF-1.

The effect of TGF-β on IL-6 expression highlights another difference between astrocytes and microglia. In microglia, TGF-β alone has no effect on IL-6 protein expression, but inhibits LPS-induced IL-6 expression (30). This is in contrast to what was observed in the astrocyte (Table II). It was previously determined that microglia do not express IL-6 in response to IL-1β or TNF-α (22), although they have functional receptors for these cytokines (56). Taken together, these findings demonstrate that IL-6 production by astrocytes and microglia is differentially modulated by TGF-β, IL-1β and TNF-α.

In vivo experiments suggest that TNF-α expression correlates with the clinical manifestations of EAE, while recovery from EAE is associated with downregulation of TNF-α expression and upregulation of TGF-β. Khoury et al. (40) examined the cytokine profiles of Lewis rats with EAE, and the effect of oral administration of MBP, which has been shown to suppress EAE. EAE was induced by injection of MBP in adjuvant, then animals were fed with ovalbumin as a control, or MBP. Brains from ovalbumin-fed animals at the peak of clinical disease showed perivascular infiltration and expression of the cytokines IL-1, IL-8, IFN-γ and TNF-α. In contrast, in MBP orally tolerized animals, there was a marked reduction of the perivascular infiltrate, downregulation of all inflammatory cytokines, and an increase in the expression TGF-β. The same pattern was observed in the CNS of Lewis rats which had spontaneously recovered. TNF-α protein has also been detected by immunohistochemistry within inflammatory CNS lesions during both the active and relapsing disease phases of mice with chronic-relapsing EAE, and is not detectable during the recovery phase of disease (57).

As mentioned previously, there are a number of endogenous CNS sources of TGF-β during disease states which include activated astrocytes, microglia and oligodendrocytes, as well as infiltrating T-cells (28, 29, 35, 58). TGF-β within the CNS acts on microglia (30) and astrocytes to inhibit TNF-α production, which in turn, prevents infiltration of inflammatory cells into the CNS, intracerebral immune responses, cytokine production, astrogliosis, and demyelination, all pathogenic events involved in immune-mediated CNS disorders such as MS and EAE. The finding that TGF-β induces IL-6 production by astrocytes is intriguing in that IL-6 may act to inhibit TNF-α production by astrocytes as it does in monocytes (25). TGF-β plays an important role in regulating cytokine cascades within the CNS, and exerts a beneficial effect by inhibiting TNF-α production by astrocytes, either directly or indirectly via IL-6.

MODES FOR CARRYING OUT THE INVENTION

Figure 1A:
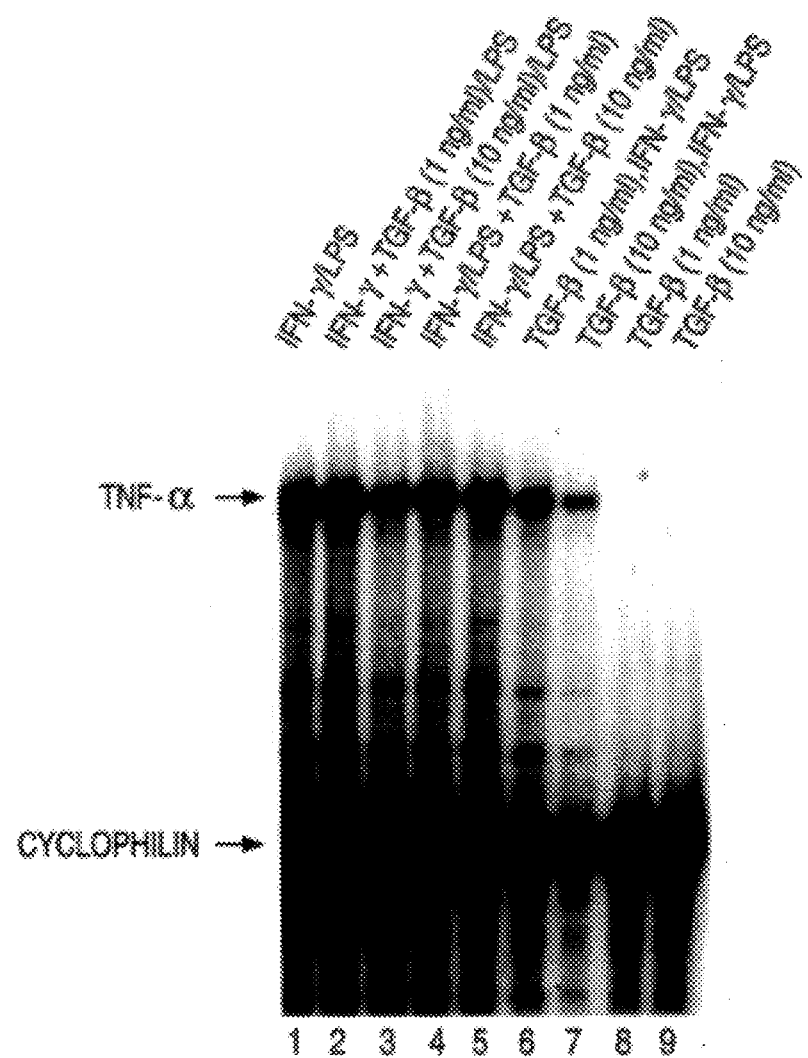
FIGS. 1A–B. TGF-β Inhibits IFN-γ/LPS Induced TNF-α mRNA Expression. Astrocytes were incubated with TGF-β (1–10 ng/ml) for 10 hours (lanes 8–9); IFN-γ (100 U/ml) for 10 hours, then LPS (1 µg/ml) for 2 hours (lane 1); IFN-γ plus TGF-β for 10 hours, then LPS for 2 hours (lanes 2–3); IFN-γ for 10 hours, then LPS plus TGF-β for 2 hours (lanes 4–5); or TGF-β for 10 hours, IFN-γ for 10 hours, then LPS for 2 hours (lanes 6–7). Total RNA was then isolated and analyzed by RNase protection assay. RNA samples were hybridized to both TNF-α and cyclophilin probes (FIGS. 1A). Quantitation of the data shown above (FIG. 1B). Representative of four experiments.

Definitions:

As used herein, the term "pro-inflammatory cytokine" means IL-1, IL-2, IL-3, IL-4, IL-5, IL-7, IL-8, IL-9, IL-11, IL-12, TNF$\alpha$, TNF$\beta$, interferon $\gamma$, GCSF, GMCSF or MCSF.

As used herein, the term "anti-inflammatory cytokine" means IL-6, IL-10, interferon $\alpha$ or interferon $\beta$.

As used herein, the term "TGF-$\beta$" includes all types of TGF-$\beta$ including TGF-$\beta$1, TGF-$\beta$2 and TGF-$\beta$3.

Abbreviations:

CNS: central nervous system; EAE: experimental allergic encephalomyelitis; GFAP: glial fibrillary acidic protein; MBP: myelin basic protein; MS: multiple sclerosis; PKC: protein kinase C; RPA: ribonuclease protection assay; TK: tyrosine kinase.

Materials and Methods:

Primary Glial Cell Cultures. Primary glial cell cultures were established from neonatal rat cerebra as described previously (14). Meninges were removed prior to culture. Culture medium was Dulbecco's modified Eagle's medium (DMEM), high glucose formula supplemented with glucose to a final concentration of 6 g/l, 2 mM glutamine, 0.1 mM nonessential amino acid mixture, 0.1% gentamicin, and 10% fetal bovine serum (FBS) (HyClone Laboratories, Logan, Utah). Oligodendrocytes were separated from the glial cultures by mechanical dislodging after 14 days in primary culture, and then the astrocytes were obtained by trypsinization (0.25% trypsin, 0.02% EDTA). The astrocytes were stained for GFAP, an intracellular antigen unique to astrocytes, using a monoclonal antibody to GFAP (1:4) for 30 minutes at room temperature, followed by a 30-minute incubation with goat anti-mouse Ig-FITC (1:20). Astrocyte cultures were routinely >97% positive for GFAP.

Reagents. Human recombinant IL-1$\beta$ (specific activity: $5\times10^8$ U/mg) was from Genzyme (Cambridge, Mass.), rat recombinant IFN-$\gamma$ (specific activity: $4\times10^6$ U/mg) was obtained from Gibco/BRL (Gaithersburg, Md.), and human recombinant TNF-$\alpha$ (specific activity: $5.6\times10^7$ U/mg) was the generous gift of Genentech, Inc. (South San Francisco, Calif.). Human recombinant TGF-$\beta_1$ and simian recombinant TGF-$\beta_2$ were the gifts of Dr. Richard Ransohoff (Cleveland Clinic, Cleveland, Ohio) and Dr. Joseph Carlino (Celtrix Pharmaceuticals, Santa Clara, Calif.), respectively. Actinomycin D-mannitol (ACT-D), MTT [3-(4,5)-dimethylthiazol-1-YL)-2,5-diphenyl-tetrazolium bromide], and LPS (*E. coli:* 0127:B8) were purchased from Sigma Chemical Co. (St. Louis, Mo.).

EXAMPLE 1: Cytokine Production by Astrocytes

Primary rate astrocytes were resuspended in DMEM containing 10% FBS, and plated at $1.0\times10^6$ cells/well into 6-well (35-mm) plates (Costar, Cambridge, Mass.). The plates were incubated overnight to allow recovery of the cells from trypsinization and to assure adherence of the astrocytes. When the astrocytes reached confluency (1–2 days after plating), the original medium was aspirated off, and 2 ml of serum-free DMEM was added to the wells. Astrocytes were treated with LPS (0–10 µg/ml), recombinant rat IFN-$\gamma$ (0–100 U/ml), recombinant human IL-1$\beta$ (0–1 ng/ml), recombinant TNF-$\alpha$ (0–100 ng/ml), recombinant TGF-$\beta$ (0–10 ng/ml), or a combination of the above for various time periods. In order to induce cytokine production in astrocytes, a number of strategies were employed which included the simultaneous addition of different agents or pretreatment with one agent prior to the addition of another. Supernatants were collected, centrifuged to remove contaminating cells, and stored at –70° C. until use.

EXAMPLE 2: Measurement of TNF-$\alpha$ Activity

TNF-$\alpha$ activity in culture supernatants was determined in a biologic assay using WEHI 164 clone 13 mouse fibrosarcoma cells as previously described (14). TNF-$\alpha$ activity was expressed as pg TNF-$\alpha$/ml culture supernatant. The absolute concentration of TNF-$\alpha$ (pg/ml) was determined by extrapolation from the standard curve which was generated by using known amounts of recombinant human TNF-$\alpha$. The lower levels of TNF-$\alpha$ sensitivity in our assay system ranged from 4–20 pg TNF-$\alpha$/ml. All samples were tested in triplicate.

EXAMPLE 3: Measurement of IL-6 Activity

IL-6 activity in astrocyte culture supernatants was determined in a biologic assay using the IL-6 dependent B cell hybridoma B9 as previously described (22). Briefly, B9 cells ($2\times10^3$ cells/well) were plated in 96-well microtitration plates; serial dilutions of astrocyte conditioned medium and recombinant murine IL-6 (used as a standard) were added, and incubated at 37° C. for 72 h. Triplicate cultures were set up for each condition. After this incubation, B9 cell growth was assessed using the MTT assay. In this assay, one unit of IL-6 is defined as the amount of IL-6 that produces a response equivalent to that achieved with 1 U of recombinant murine IL-6.

EXAMPLE 4: RNA Isolation, Riboprobes, and RNase Protection Assay

Primary astrocytes were plated as described above for protein experiments except at $5\times10^6$ cells per 100-mm$^2$ dish. Total cellular RNA was isolated from resulting confluent monolayers of astrocytes that had been incubated with various reagents. RNA isolation was performed as previously described (14). Briefly, cells were scraped and washed two times in PBS, and pelleted. RNA was extracted with guanidinium isothiocyanate and phenol, and precipitated with ethanol. Levels of RNA were analyzed by RNase protection assay (RPA) as described below.

A 672-bp BamHI/AccI fragment of the pBS vector containing a rat IL-6 cDNA (ATCC, Rockville, Md.) was subcloned into the BamHI/AccI polylinker site of pGEM-4Z (Promega, Madison, Wis.). The construct was linearized by BglII and radiolabeled antisense RNA of 466 nt was generated from the linearized plasmid by in vitro transcription as previously described (23). A 717-bp PstI/BamHI fragment of pUC119 containing a partial rat TNF-$\alpha$ cDNA was subcloned into the PstI/BamHI polylinker site of pGEM-3Z. The construct was linearized by XhoI, and the linearized plasmid was used to generate a radiolabeled antisense RNA 485 nt in length by in vitro transcription as previously described (16). A pBS vector containing a fragment of rat cyclophilin cDNA was a gift from Dr. G. Fuller (University of Alabama at Birmingham). As previously described, a 271 nt cyclophilin antisense riboprobe was also synthesized from the cyclophilin-containing pBS vector which had been linearized by NcoI (42).

In vitro transcription was performed with the T7 in vitro transcription kit (Ambion, Austin, Tex.) as previously described (16), in a final volume of 20 µl containing 40 mM Tris-HCl, pH 7.5, 6 mMMgCl$_2$, 2 mM spermidine, 10 mM NaCl, 500 mM ATP, CTP, and GTP, 10 mM DDT, 25 U of ribonuclease inhibitor, 12.5 µM of [$\alpha$-$^{32}$P] UTP (800 Ci/mmol, 40 mCi/ml) (NEN), 1 µg of linearized DNA, and 10 U of T7 RNA polymerase at 2°–4° C. for 60 minutes. The resulting radiolabeled rat TNF-α, IL-6 and cyclophilin transcripts were then purified by electrophoresis in 5% polyacrylamide/8M urea gels, excised from the gel following a brief X-ray film exposure for localization, and eluted overnight at 37° C. in 350 μl elution buffer containing 0.5M NH₄OAc, 1 mM EDTA and 0.1% SDS.

RPA was carried out with an RPA kit according to the manufacturer's instructions (Ambion, Austin, Tex.), as previously described (16). Twenty μg of total RNA from astrocytes was hybridized with both IL-6 and cyclophilin riboprobes, or TNF-α and cyclophilin riboprobes (1×10⁵ cpm each) at 45° C. overnight in 20 μl of 40 mM PIPES pH 6.4, 80% deionized formamide, 400 mM NaOAc, and 1 mM EDTA. The hybridized mixture was then treated with RNase A/T1 (1:100 dilution in 200 vl of the RNase digestion buffer) at 37° C. for 30 min and analyzed by 5% denaturing (8M urea) polyacrylamide gel electrophoresis. The fragments of the IL-6, TNF-α, and cyclophilin riboprobes which are protected from RNase are 437 nt, 445 nt, and 221 nt in length, respectively. A Phosphorimager (Molecular Dynamics, Sunnyvale, Calif.) was used to quantitate protected fragments, and values given for IL-6 and TNF-α mRNA induction were normalized to cyclophilin mRNA expression, which is not affected by the treatments used in these experiments.

EXAMPLE 5: Nuclear Run-On Analysis

Nuclear run-on assays were performed as previously described (16). Nuclei were isolated from confluent monolayers of astrocytes that were incubated for various times with IFN-γ, LPS, TNF-α and/or TGF-β. The cells (4–6×10⁷) were collected, washed twice with cold PBS and pelleted. Nuclei were isolated by lysing the cells in 0.01M Tris (pH 8.4), 1.5 mM MgCl₂, 0.14M NaCl and 5% Nonidet P40 (NP40) followed by centrifugation at 1000 x g. The nuclei were stored at −70° C. in buffer containing 0.02M Tris (pH 8.0), 20% glycerol, 0.14M KCl, 10 mM MgCl₂, 1 mM MnCl₂, and 14 mM β-mercaptoethanol. To perform run-on transcriptional analysis, the nuclei were thawed on ice and incubated for 30 minutes at 30° C. in reaction buffer containing 0.033M each of ATP, GTP, and CTP, 2.5 x storage buffer and 0.5 mCi of ³²P-UTP (3000 Ci/mM, Amersham Corp., Arlington Heights, Ill.). After the reaction, nuclei were lysed with guanidine thiocyanate and the DNA sheared using a 22 gauge needle. Samples were loaded onto a cushion of 5.7M CsCl, 0.01M EDTA (pH 7.5), and spun at least 16 hours at 36,000 rpm at 20° C. RNA pellets were recovered, partially digested by hydrolysis with 1M NaOH, neutralized with 1M Hepes, and labeled transcripts were purified by ethanol precipitation. Denatured circular plasmid DNA was immobilized onto nitrocellulose paper using a Millipore (Bedford, Mass.) Milliblot S system. After U.V. crosslinking the DNA to the nitrocellulose, prehybridization was performed at 65° C. for at least 3 hours in a solution of 10 mM Tris (pH 8.0), 10 mM EDTA, 300 mM NaCl, 1.0 mg/ml Ficoll, 1.0 mg/ml polyvinylpyrrolidone, 1 mg/ml BSA, and 100 U/ml RNasin (Promega Biotech, Madison, Wis.). For hybridization, 2×10⁷ cpm of labeled RNA was used in 2 ml of hybridization solution and incubated at 65° C. for 48–72 hours. The filters were washed in 2X SSC for 10 minutes at room temperature, 50 minutes at 65° C., 30 minutes at 37° C. in 2X SSC with 10 mg/ml ribonuclease A, and finally for 30 minutes at 37° C. in 2X SSC. The filters were exposed to the Phosphorimager (Molecular Dynamics) for quantitation. The "inhibition" or "stimulation" of transcriptional activation was determined by comparing the ratios of TNF-α/cyclosphilin or IL-6/cyclophilin, respectively, for each stimulus.

EXAMPLE 6: TGF-β Inhibits TNF-α Gene Expression by Astrocytes

We have previously demonstrated that rat astrocytes secrete TNF-α protein in response to LPS alone, IFN-γ plus LPS, and IFN-γ plus IL-1β (14, 16). IFN-γ alone does not induce TNF-α production by astrocytes, but acts to enhance LPS-induced TNF-α synthesis and to synergize with IL-1β for TNF-α production. The most potent TNF-α production is observed when astrocytes are pretreated with IFN-γ for 8–12 hours prior to exposure to either LPS or IL-1β, suggesting the IFN-γ provides a priming signal to the astrocyte. The effect of TGF-β on TNF-α expression was assessed in this study. Astrocytes were incubated with TGF-β (1.0–10 ng/ml) alone for 15 hours, at which time TNF-α protein production was examined. TGF-β itself did not influence TNF-α production by astrocytes (Table 1). However, TGF-β, in a dose-dependent manner, inhibited IFN-γ/LPS induced TNF-α production. The magnitude of inhibition was dependent on when the cells were exposed to TGF-β; i.e., astrocytes treated with TGF-β prior to the inducing stimuli were suppressed to the greatest degree, compared to when TGF-β was added simultaneously with the inducing stimuli (Table I). Comparable results were obtained using the stimulus of IFN-γ/IL-1β (data not shown). TGF-β₁ and TGF-β₂ were equally effective at inhibiting TNF-α expression (data not shown).

TABLE I

TGF-β Inhibits Production of TNF-α by Astrocytes

| Cell Treatment | TNF-α Activity[a] (pg/ml/1 × 10⁶ cells) | % inhibition[i] |
|---|---|---|
| Control[b] | 0[h] | |
| TGF-β (ng/ml)[c] 1.0 | 0 | |
| 10.0 | 0 | |
| IFN-γ/LPS[d] | 843 ± 167 | |
| IFN-γ/LPS + TGF-β[e] 1.0 | 639 ± 54 | 25% |
| 10.0 | 421 ± 89 | 50% |
| IFN-γ + TGF-β/LPS[f] 1.0 | 478 ± 39 | 43% |
| 10.0 | 319 ± 76 | 62% |
| TGF-β, IFN-γ/LPS[g] 1.0 | 204 ± 66 | 76% |
| 10.0 | 103 ± 15 | 88% |

Figure 1B:
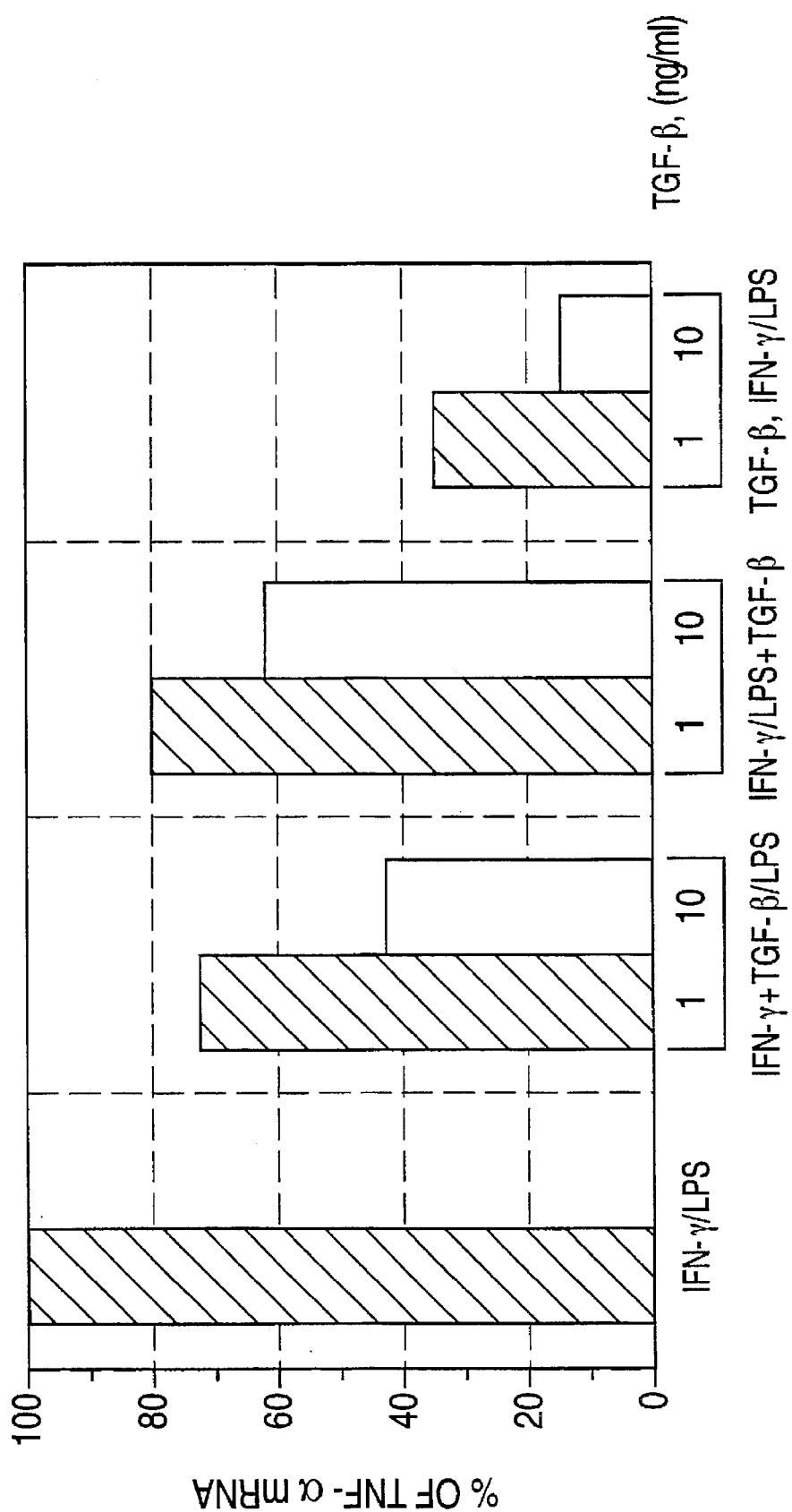

[a]TNF-α activity assessed by WEHI bioassay
[b]Culture medium alone for 18 h
[c]TGF-β1 for 18 h
[d]IFN-γ (100 U/ml) for 10 h, then LPS (1 μg/ml) for 8 h
[e]IFN-γ (100 U/ml) for 10 h, then LPS (1 μg/ml) plus TGF-β for 8 h
[f]IFN-γ (100 U/ml) plus TGF-β for 10 h, then LPS (1 μg/ml) for 8 h
[g]TGF-β for 10 h; IFN-γ (100 U/ml) for 10 h, then LPS (1 μg/ml) for 8 h
[h]Mean ± S.D. of two experiments
[i]% inhibition is compared to IFN-γ/LPS value To determine if the inhibitory effect of TGF-β was mediated at the mRNA level, RPA was performed. Astrocytes were treated with combinations of IFN-γ, LPS and TGF-β for varying time periods, and total cellular RNA was harvested and analyzed. As shown in FIG. 1A, no mRNA for TNF-α is detected in TGF-β treated cells (lanes 8 and 9), and TGF-β inhibits IFN-γ/LPS induced TNF-α mRNA expression. Similar to what was observed at the TNF-α protein level, the degree of inhibition of TNF-α mRNA expression was dependent upon time of exposure to TGF-β. FIG. 1B presents the quantitation of the blot shown in FIG. 1A; inhibition of TNF-α mRNA was most pronounced in astrocytes which had been pretreated with TGF-β, then exposed to IFN-γ/LPS (lanes 6 and 7).

Figure 2A:
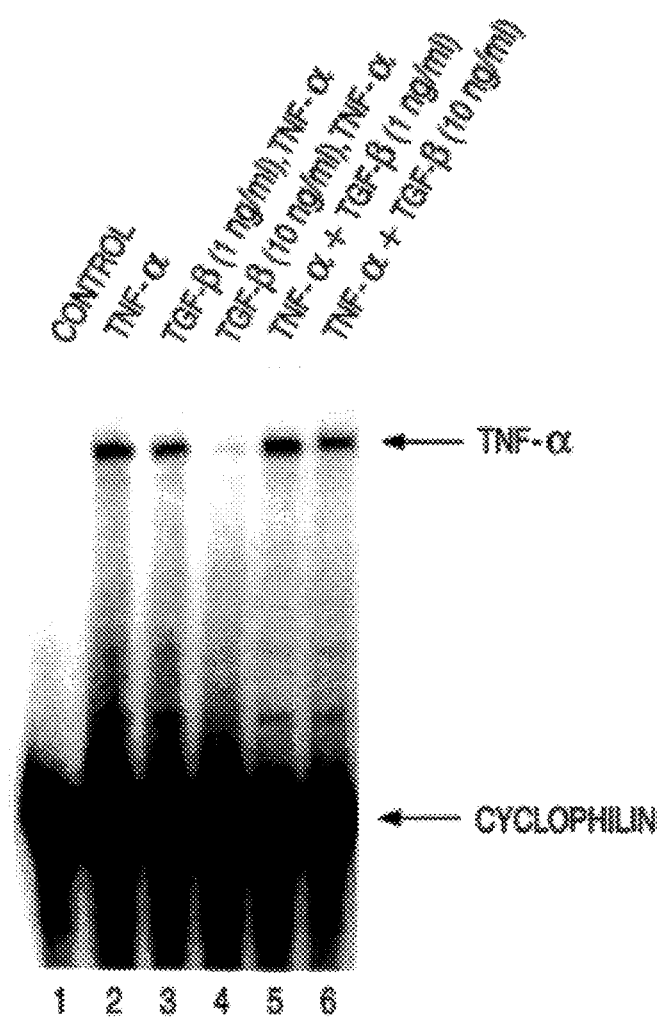
FIGS. 2A–B. TGF-β Inhibits TNF-α Induced TNF-α mRNA Expression. Astrocytes were incubated with medium alone (lane 1); TNF-α (50 ng/ml) for 2 hours (lane 2); TGF-β for 10 hours, then TNF-α for 2 hours (lanes 3–4); or TNF-α plus TGF-β for 2 hours (lanes 5–6). Total RNA was then isolated and analyzed by RNase protection assay. RNA samples were hybridized to both TNF-α and cyclophilin probes (FIG. 2A). Quantitation of the data shown above (FIG. 2B). Representative of three experiments.
Figure 2B:
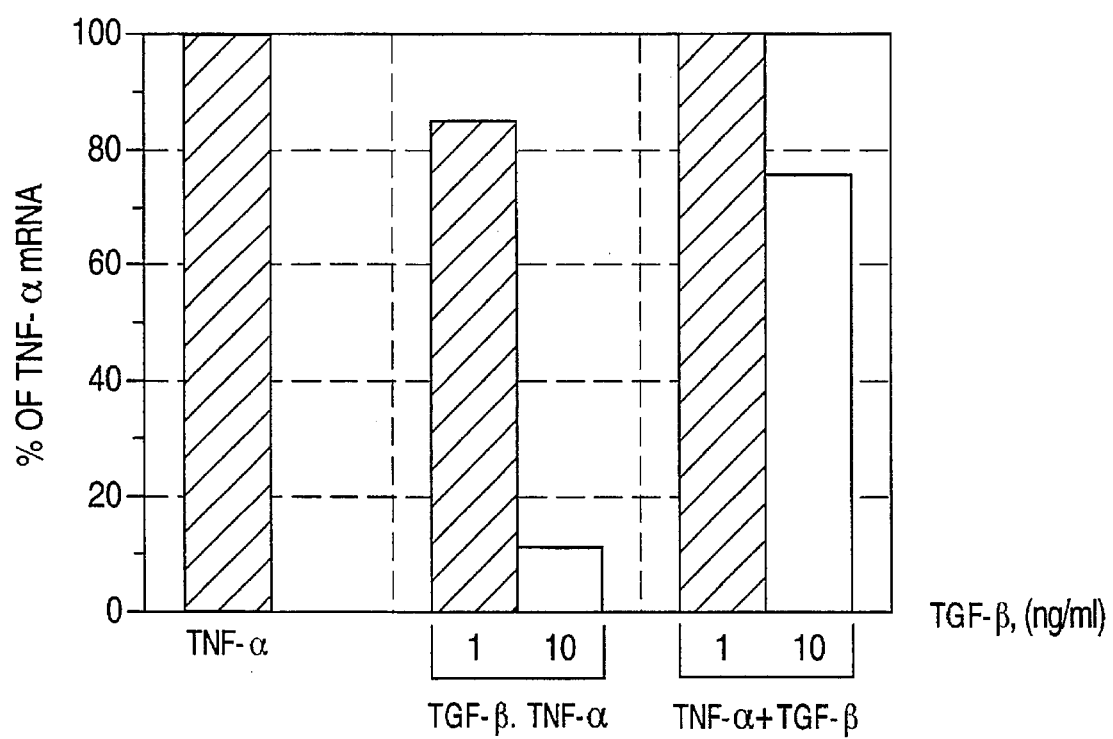
Figure 3A:
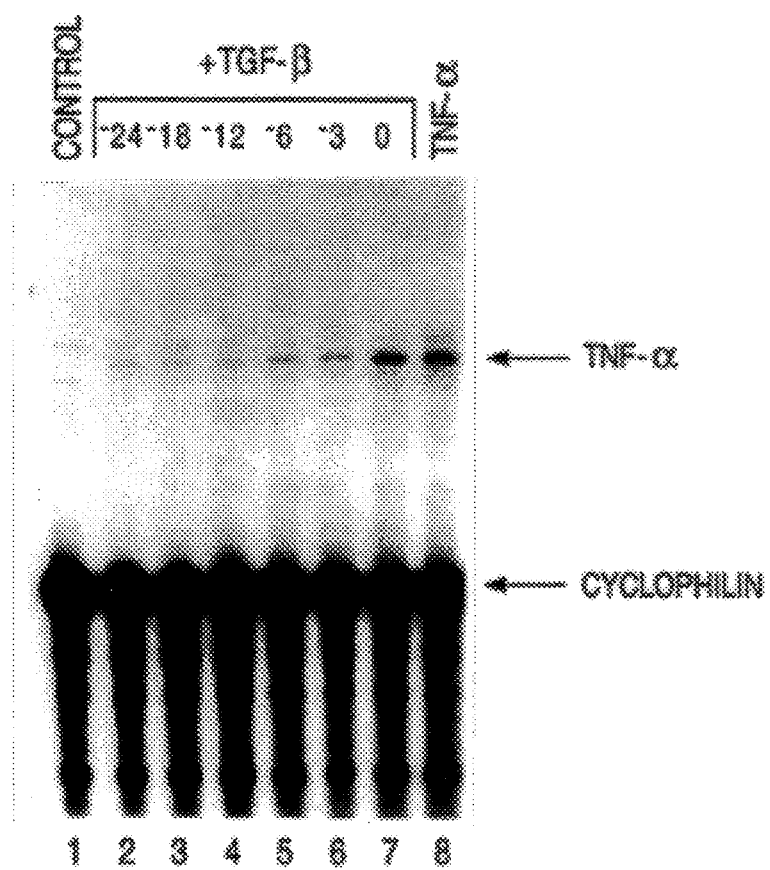
FIGS. 3A–B. Kinetic Analysis of the Inhibitory Effect of TGF-β. Astrocytes were incubated with medium alone (lane 1); TNF-α (50 ng/ml) for 2 hours (lane 8); or with TGF-β (10 ng/ml) for varying time periods before exposure to TNF-α, or simultaneously with TNF-α (lanes 2–7). RNA samples were hybridized to both TNF-α and cyclophilin probes (FIG. 3A). Quantitation of the data shown above (FIG. 3B). Representative of three experiments.
Figure 3B:
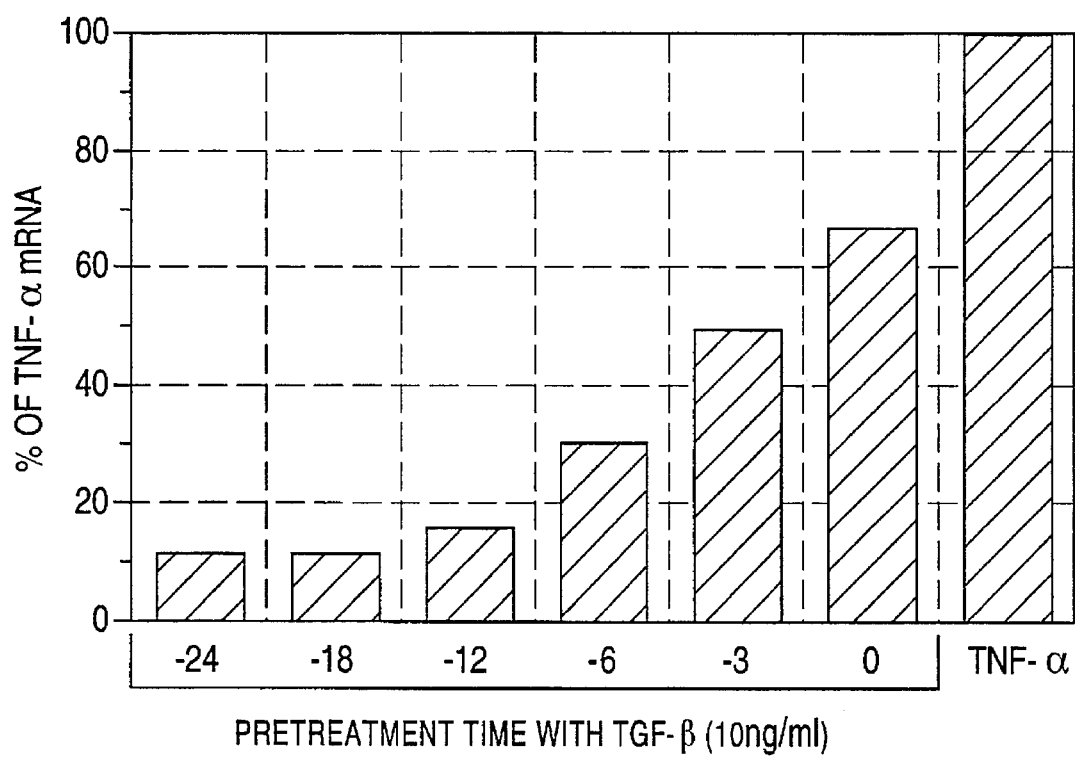

Since astrocytes are capable of producing TNF-α and express receptors for this cytokine, we wished to determine if TNF-α could act to induce its own gene. As shown in FIG. 2A, TNF-α (50 ng/ml) induces expression of TNF-α mRNA in astrocytes (lane 2). Dose-response studies using TNF-α at 0.5–100 ng/ml show that 50 ng/ml of TNF-α is optimal for inducing TNF-α mRNA expression (data not shown). TGF-β inhibits this expression, and inhibition of TNF-α mRNA is most pronounced when the cells were pretreated with TGF-β for 10 hours, then exposed to TNF-α (lanes 3 and 4), compared to when TGF-β and TNF-α were added simultaneously (lanes 5 and 6). Quantitation of the blot is shown in FIG. 2B. To examine the kinetics of TGF-β mediated inhibition, experiments were initiated in which astrocytes were exposed to TGF-β (10 ng/ml) for 3–24 hours prior to TNF-α, or simultaneously with TNF-α, when RNA was extracted and analyzed by RPA. As shown in FIG. 3, inhibition of TNF-α mRNA was observed when astrocytes were pretreated with TGF-β, with optimal inhibition observed at 12–18 hours (85–89% inhibition).

EXAMPLE 7: Stability of TNF-α mRNA in Astrocytes Exposed to TNF-α and TGF-β

Figure 4A:
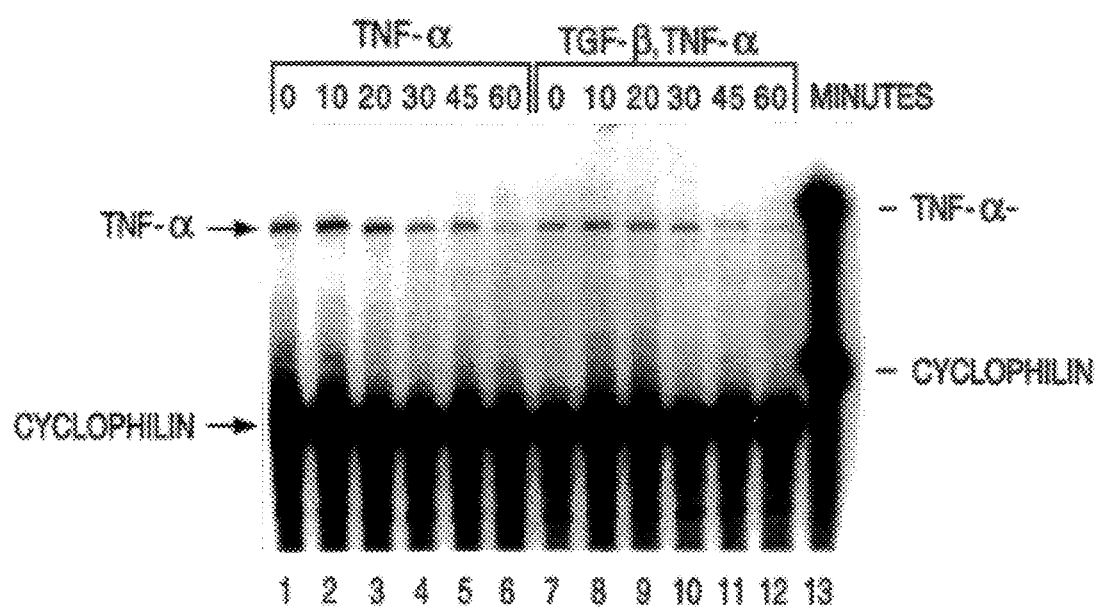
FIGS. 4A–B. TNF-α mRNA t ½ in Rat Astrocytes Treated with either TNF-α or TGF-β plus TNF-α. Cells were incubated with TNF-α (50 ng/ml) for 2 hours, or TGF-β (10 ng/ml) for 3 hours, then TNF-α for 2 hours, then ACT-D (5 µg/ml) was added, cells harvested at the indicated times, and RNA subjected to RPA (FIG. 4A). Lane 13 is the TNF-α and cyclophilin riboprobes run without any added RNA. TNF-α values were normalized for cyclophilin hybridization within each sample. TNF-α mRNA at time 0 (prior to addition of ACT-D) was plotted as 100% (FIG. 4B). Representative of three experiments.
Figure 4B:
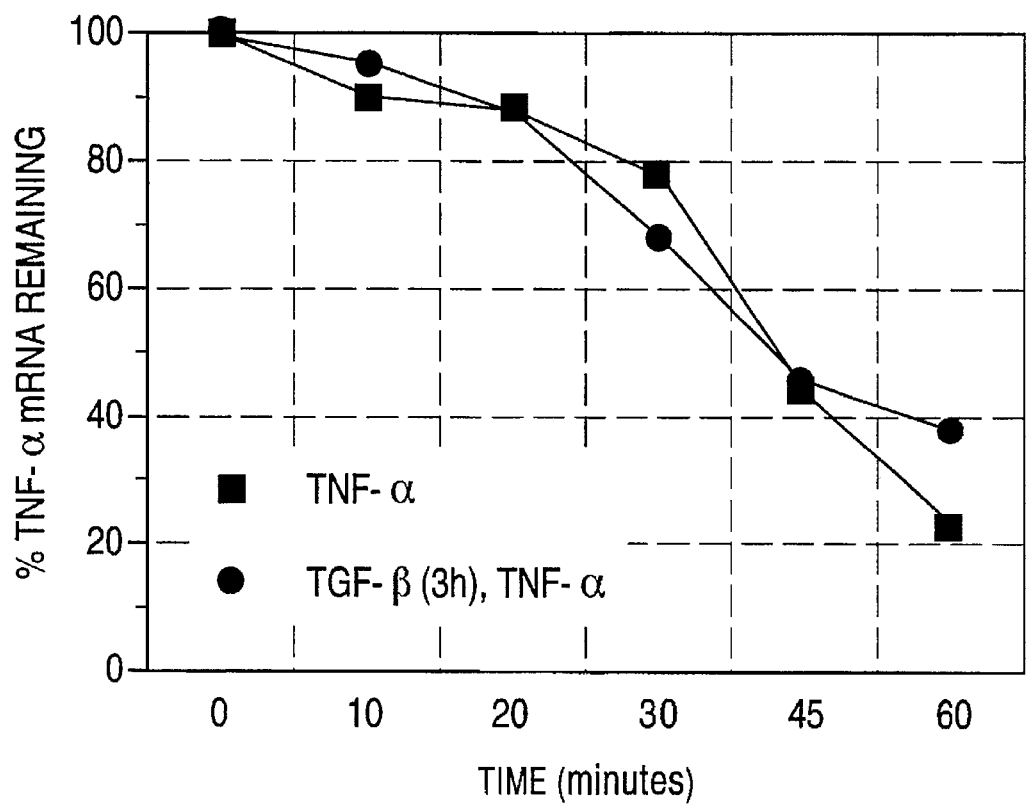

To elucidate the mechanism(s) by which TGF-β inhibits TNF-α mRNA expression, we performed experiments examining the t ½ life of TNF-α mRNA in the presence or absence of TGF-β. Astrocytes were incubated either with medium alone or with TGF-β (10 ng/ml) for 3 hours, then exposed to TNF-α (50 ng/ml) for 2 hours, and ACT-D was added for an additional 10–60 minutes. RNA was isolated at serial time points, and examined for levels of TNF-α mRNA. We chose a TGF-β preincubation time of 3 hours since we did not want to completely inhibit TNF-α mRNA expression. The t ½ of TNF-α mRNA induced by TNF-α alone was ~40 min, and that of TNF-α mRNA induced by TNF-α and TGF-β was comparable (FIG. 4). These data show that although a 3 hour preincubation with TGF-β inhibits TNF-α steady-state mRNA levels by ~50% (see FIG. 3), TGF-β has no effect on TNF-α mRNA stability. Similar results were obtained using IFN-γ/LPS or IFN-γ/IL-1β as stimuli (data not shown).

EXAMPLE 8: TGF-β Inhibits Transcription of the TNF-α Gene

Figure 5:
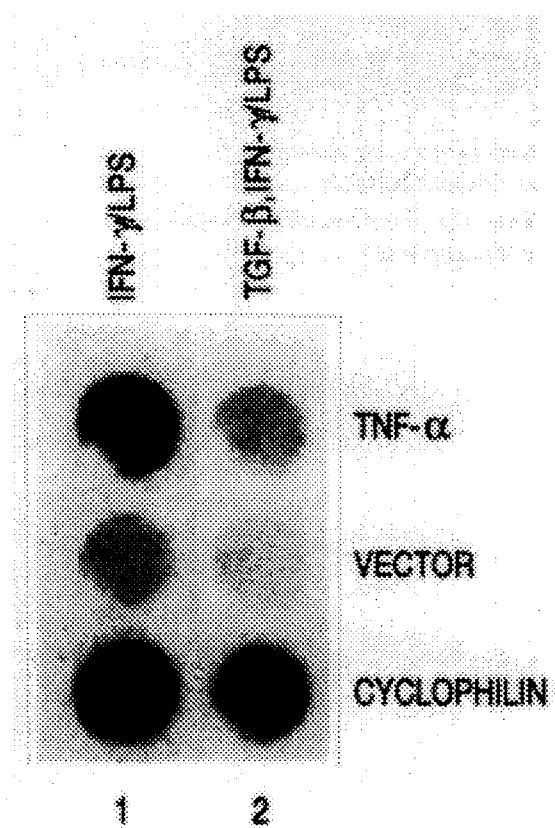
FIG. 5. TGF-β Inhibits IFN-γ/LPS Induced Transcription of the TNF-α Gene. Cells were treated with medium or TGF-β (10 ng/ml) for 12 hours, incubated with IFN-γ (100 U/ml) for 10 hours, and then with LPS (1 µg/ml) for an additional 2 hours. Labeled transcripts were prepared as described in Materials and Methods, and hybridized to filters containing 2.5 µg of rat TNF-α plasmid cDNA, vector DNA, and cyclophilin cDNA. Representative of two experiments.

We have previously demonstrated that IFN-γ/LPS and IFN-γ/IL-1β induce transcription of the TNF-α gene in astrocytes (16). We performed nuclear run-on assays to determine whether TGF-β affects TNF-α gene transcription. Astrocytes were treated with medium or TGF-β (10 ng/ml) for 12 hours, exposed to IFN-γ for 10 hours, then exposed to LPS for 2 hours, the nuclei isolated, and the RNA transcripts that had been initiated allowed to compete in the presence of [$^{32}$P] UTP. Labeled RNA transcripts were then hybridized to dot-blotted cDNA encoding either rat TNF-α or cyclophilin, or DNA vector pGEM-3Z as a negative control. The levels of TNF-α transcription were normalized to that of cyclosporin. As shown in FIG. 5, pretreatment of astrocytes with TGF-β inhibited IFN-γ/LPS-induced transcription of the TNF-α gene. Quantitation of this data shows ~70% inhibition in the presence of TGF-β. Comparable inhibition of TNF-αinduced TNF-α transcription by TGF-β was observed (data not shown).

EXAMPLE 9: TGF-β Induces and Enhances IL-6 Gene Expression by Astrocytes

Figure 6A:
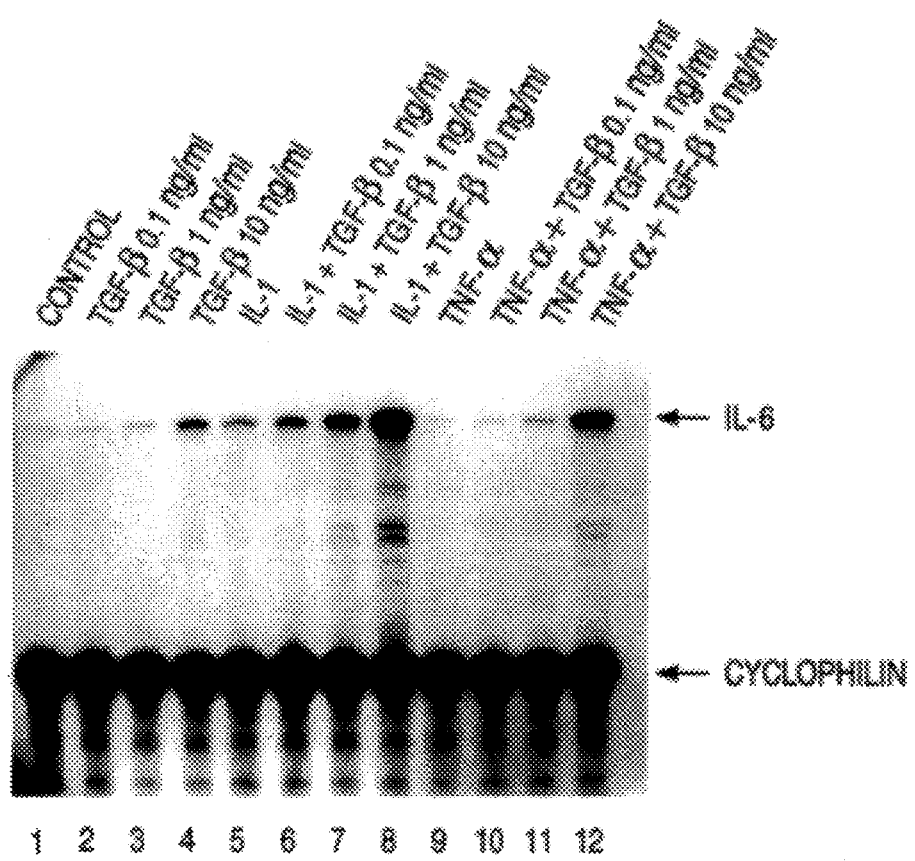
FIGS. 6A–B. TGF-β Induces and Enhances IL-6 mRNA Expression in Astrocytes. Cells were incubated with medium alone (lane 1); TGF-β (0.1–10 ng/ml) (lanes 2–4); IL-1β (1 ng/ml) (lane 5); IL-1β plus TGF-β (lanes 6–8); TNF-α (100 ng/ml) (lane 9); or TNF-α plus TGF-β (lanes 10–12) for 4 hours. Total RNA was then isolated, hybridized to both IL-6 and cyclophilin probes, and analyzed by RPA (FIG. 6A). Quantitation of the data shown above (FIG. 6B). Representative of four experiments.
Figure 6B:
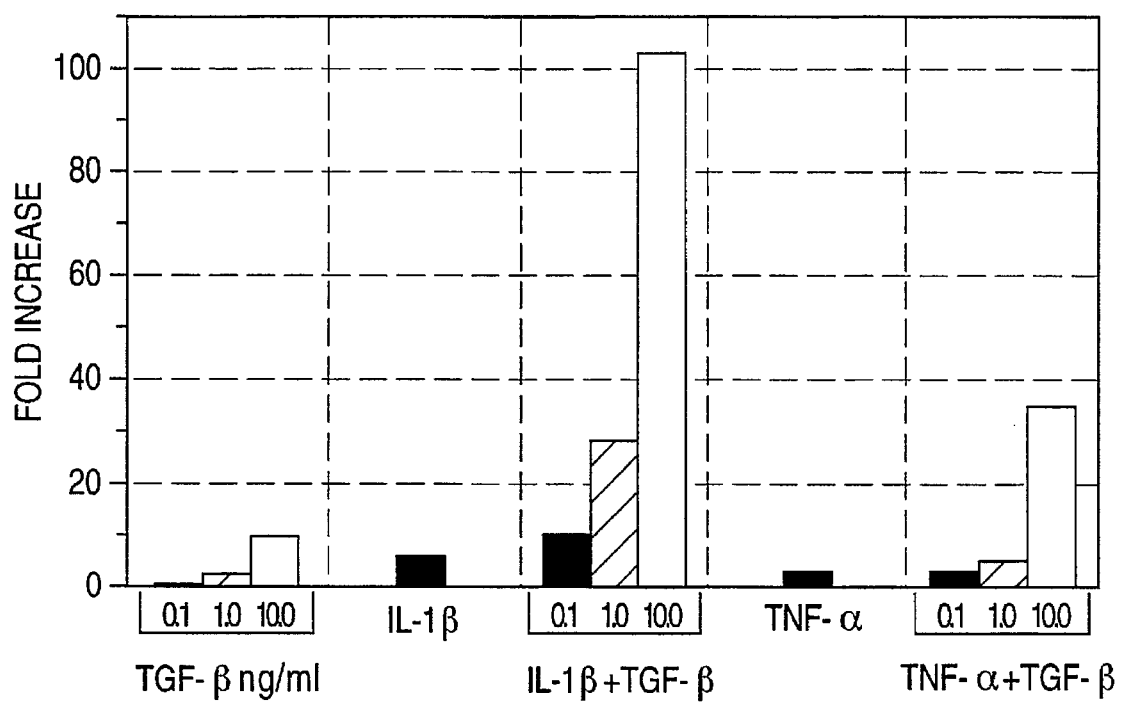

IL-1β and TNF-α are each capable of inducing IL-6 expression, and act together in a synergistic manner for enhanced IL-6 expression in astrocytes (23). We tested the effect of TGF-β on IL-6 expression either alone or in conjunction with IL-1β or TNF-α. The concentrations of IL-1β (1 ng/ml) and TNF-α (100 ng/ml) used in this study have been previously determined to be optimal for inducing IL-6 expression (23). TGF-β, in a dose-dependent manner, induced IL-6 protein, and synergized with IL-1β or TNF-α for enhanced IL-6 expression in astrocytes (Table II). Comparable findings were observed at the mRNA level, where TGF-β alone induces IL-6 mRNA expression (FIG. 6A, lanes 2–4), and synergizes with either IL-1β or TNF-α for enhanced IL-6 expression (lanes 5–12). Quantitation of this blot indicates that for TGF-β enhancement of IL-1β-induced IL-6, an additive effect was observed at the lowest concentration of TGF-β used (0.1 ng/ml), with maximal enhancement seen using 10 ng/ml of TGF-β (FIG. 6B). For TGF-β enhancement of TNF-α-induced IL-6 expression, a slight additive effect was observed using TGF-β at 1 ng/ml, with a synergistic effect obtained using 10 ng/ml of TGF-β. A consistent observation was that TGF-β was a more potent enhancer of IL-1α-induced IL-6 expression, compared to TNF-α. Both TGF-$\beta_1$ and TGF-$\beta_2$ were effective in this system.

EXAMPLE 10: Stability of IL-6 mRNA in Astrocytes Exposed to TGF-β, TNF-α, and IL-1β

Figure 7A:
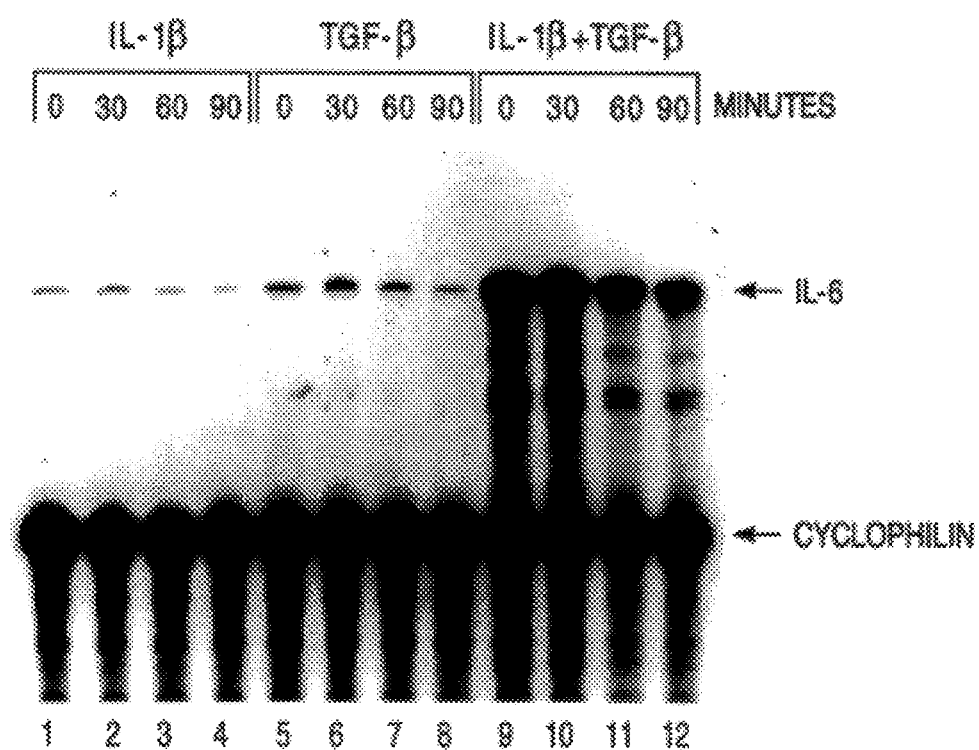
FIGS. 7A–D. IL-6 mRNA t ½ in Rat Astrocytes Treated With Various Cytokines. Cells were incubated with IL-1β (1 ng/ml); TGF-β (10 ng/ml); or IL-1β plus TGF-β for 4 hours, then ACT-D (5 µg/ml) was added, cells harvested at the indicated times, and RNA subjected to RPA. The gel was exposed to film for 1 day (FIG. 7A). Cells were incubated with TNF-α (100 ng/ml); TGF-β; or TNF-α plus TGF-β for 4 hours, then treated as described above. The gel was exposed to film for 4 days. A longer exposure time was used since TNF-α is a weaker inducer of IL-6 mRNA expression than IL-1β (FIG. 7B). Quantitation of the data shown above (FIGS. 7C and 7D). Representative of three experiments.
Figure 7B:
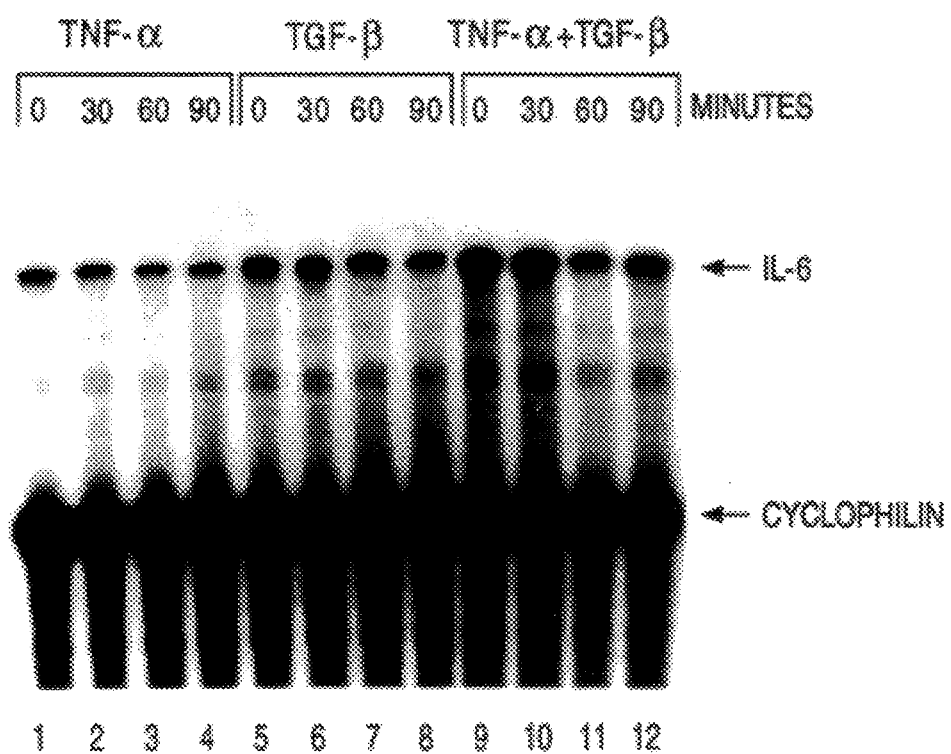
Figure 7C:
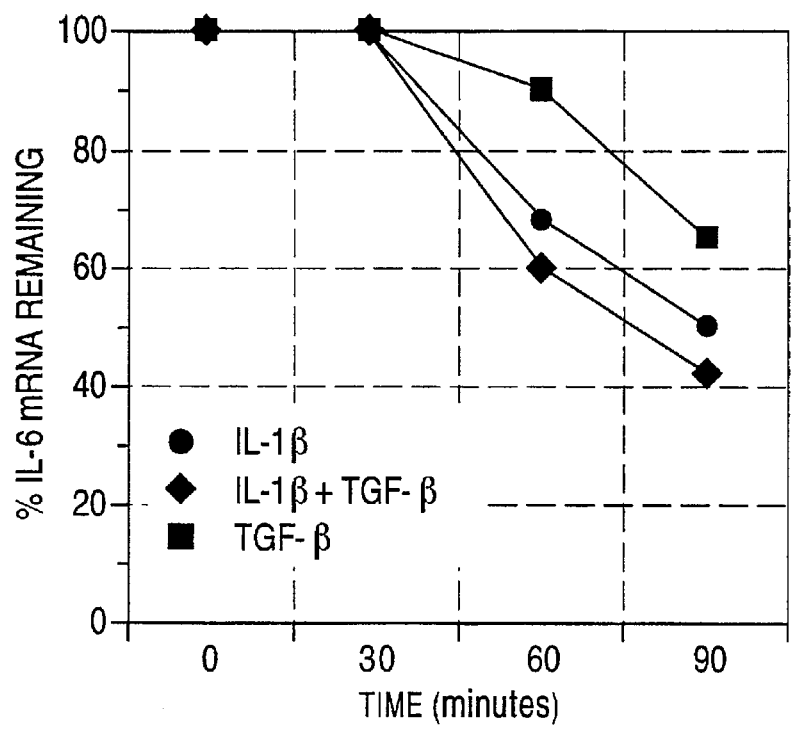
Figure 7D:
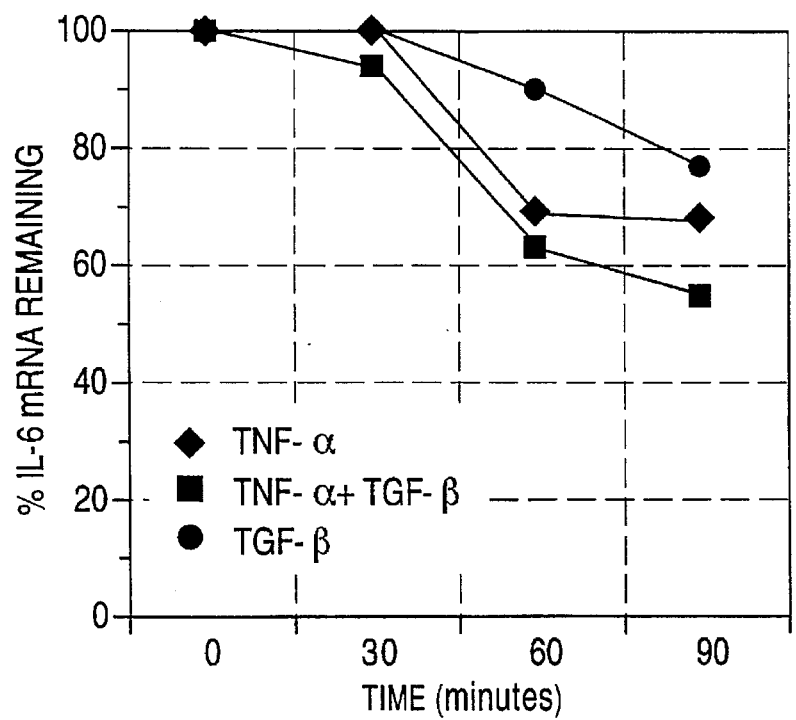

To determine if TGF-β exerted its enhancing effect on IL-1β or TNF-α-induced IL-6 mRNA expression by stabilization of the IL-6 message, t ½ life experiments were performed. Astrocytes were incubated with IL-1β, TGF-β, IL-1β plus TGF-β, TNF-α, or TNF-α plus TGF-β for 4 hours, and ACT-D was added for an additional 30–90 minutes. RNA was isolated at these serial time points, and examined for levels of IL-6 mRNA. The t ½ life of IL-6 mRNA induced by IL-1β was ~90 minutes, that for TGF-β-induced IL-6 ~100 minutes, and that of IL-1β plus TGF-β-induced IL-6 ~80 minutes (FIGS. 7A, 7C). A similar finding was observed for TNF-α-induced IL-6 mRNA expression; the t ½ life was not prolonged by TGF-β (FIGS. 7B and 7D). Longer time points after ACT-D addition have been examined (up to 135 minutes), with comparable results (data not shown). These results demonstrated that TGF-β does not promote stabilization of IL-1β or TNF-β-induced IL-6 message, suggesting its effect on IL-6 mRNA steady-state levels is not mediated at the post-transcriptional level. This predication was borne out by nuclear run-on assays demonstrating the TGF-β alone induces transcription of the IL-6 gene, and synergizes with both IL-1β and TNF-α to enhance IL-6 gene transcription (data not shown).

References
1. Beutler, B. and A. Cerami, 1989. The biology of cachectin/TNF-A primary mediator of the host response. Annu. Rev. Immunol. 7:625.
2. Selmaj, K. W. and C. S. Raine. 1988. Tumor necrosis factor mediates myelin and oligodendrocyte damage in vitro. Ann. Neurol. 23:339.
3. Robbins, D. S., Y. Shirazi, B. E. Drysdale, A. Lieberman, H. S. Shin, and M. L. Shin. 1987. Production of cytotoxic factor for oligodendrocytes by stimulated astrocytes. J. Immunol. 139:2593.
4. Raine, C. S. 1984. Biology of disease: Analysis of autoimmune demyelination: Its impact upon multiple sclerosis. Lab. Invest. 50:608.
5. Selmaj, K. W., M. Farooq, W. T. Norton, C. S. Raine, and C. F. Brosnan. 1990. Proliferation of astrocytes in vitro in response to cytokines. A primary role for tumor necrosis factor. J. Immunol. 144:129.

6. Panek, R. B., H. Moses, J. P.-Y. Ting, and E. N. Benveniste. 1992. Tumor necrosis factor α response elements in the HLA-DRA promoter: Identification of a tumor necrosis factor α-induced DNA-protein complex in astrocytes. Proc. Natl. Acad. Sci. USA 89:11518.

7. Benveniste, E. N. 1992. Inflammatory cytokines within the central nervous system: sources, function, and mechanism of action. Am. J. Physiol.:Cell Physiol. 263:32:C1.

8. Hofman, F. M., D. R. Hinton, K. Johnson, and J. E. Merrill. 1989. Tumor necrosis factor identified in multiple sclerosis brain. J. Exp. Med. 170:607.

9. Selmaj, K., C. S. Raine, B. Cannella, and C. F. Brosnan. 1991. Identification of lymphotoxin and tumor necrosis factor in multiple sclerosis lesions. J. Clin. Invest. 87:949.

10. Sharief, M. K., M. Phil, and R. Hentges. 1991. Association between tumor necrosis factor-α and disease progression in patients with multiple sclerosis. N. Engl. J. Med. 325:467.

11. Sharief, M. K., M. A. Noori, M. Ciardi, A. Cirelli, and E. J. Thompson. 1993. Increased levels of circulating ICAM-1 in serum and cerebrospinal fluid of patients with active multiple sclerosis. Correlation with TNF-α and blood-brain barrier damage. J. Neuroimmunol. 43:15.

12. Ruddle, N. H., C. M. Bergman, K. M. McGrath, E. G. Lingenheld, M. L. Grunnet, S. J. Padula, and R. B. Clark. 1990. An antibody to lymphotoxin and tumor necrosis factor prevents transfer of experimental allergic encephalomyelitis. J. Exp. Med. 172:1193.

13. Selmaj, K., C. S. Raine, and A. H. Cross. 1991. Anti-tumor necrosis factor therapy abrogates autoimmune demyelination. Ann. Neurol. 30:694.

14. Chung, I. Y. and E. N. Benveniste. 1990. Tumor necrosis factor-α production by astrocytes: Induction by lipopolysaccharide, IFN-γ and IL-1β. J. Immunol. 144:2999.

15. Lieberman, A. P., P. M. Pitha, H. S. Shin, and M. L. Shin. 1989. Production of tumor necrosis factor and other cytokines by astrocytes stimulated with lipopolysaccharide or a neurotropic virus. Proc. Natl. Acad. Sci. USA 66:6348.

16. Chung, I. Y., J. Kwon, and E. N. Benveniste. 1992. Role of protein kinase C activity in tumor necrosis factor-α gene expression: Involvement at the transcriptional level. J. Immunol. 149:3894.

17. Lieberman, A. P., P. M. Pitha, and M. L. Shin. 1990. Protein kinase regulates tumor necrosis factor mRNA stability in virus-stimulated astrocytes. J. Exp. Med. 172:989.

18. Lieberman, A. P., P. M. Pitha, and M. L. Shin. 1992. Poly(A) removal is the kinase-regulated step in tumor necrosis factor mRNA decay. J. Biol. Chem. 267:2123.

19. Benveniste, E. N., I. Y. Chung, L. P. Tang, and J. Kwon. 1993. Intracellular second messengers involved in both induction and inhibition of TNF-α expression by astrocytes. J. Immunol. 150:245.

20. Fisher, S., P. Pitha, and M. Shin. 1993. Role of tyrosine kinase signalling in newcastle disease virus (NDV) mediated TNF-α gene activation in astrocytes. J. Immunol. 150:295.

21. Frei, K., U. V. Malipiero, T. P. Leist, R. M. Zinkernagel, M. E. Schwab, and A. Fontana. 1989. On the cellular source and function of interleukin-6 produced in the central nervous system in viral diseases. Eur. J. Immunol. 19:689.

22. Norris, J. G. and E. N. Benveniste. 1993. Interleukin-6 production by astrocytes: Induction by the neurotransmitter norepinephrine. J. Neuroimmunol. 45:137.

23. Norris, J. G., L.-P. Tang, S. M. Sparacio, and E. N. Benveniste. 1994. Signal transduction pathways mediating astrocyte IL-6 induction by IL-1β and tumor necrosis factor-α. J. Immunol. 152:841.

24. Hirano, T., S. Akira, T. Taga, and T. Kishimoto. 1990. Biological and clinical aspects of interleukin 6. Immunology Today 11:443.

25. Aderka, D., J. Le, and J. Vilcek. 1989. IL-6 inhibits lipopolysaccharide-induced tumor necrosis factor production in cultured human monocytes, U937 cells, and in mice. J. Immunol. 143:3517.

26. Merrill, J. E. 1992. Proinflammatory and antiinflammatory cytokines in multiple sclerosis and central nervous system acquired immunodeficiency syndrome. J. Immunother. 12:167.

27. Massague, J. 1990. The transforming growth factor-β family. Annu. Rev. Cell. Biol. 6:597.

28. da Cunha, A., J. A. Jefferson, R. W. Jackson, and L. Vitkovic. 1993. Glial cell-specific mechanisms of TGF-β1 induction by IL-1 in cerebral cortex. J. Neuroimmunol. 42:71.

29. Morganti-Kossmann, M. C., T. Kossmann, M. E. Brandes, S. E. Mergenhagen, and S. M. Wahl. 1992. Autocrine and paracrine regulation of astrocyte function by transforming growth factor-β. J. Neuroimmunol. 39:163.

30. Suzumura, A., M. Sawada, H. Yamamoto, and T. Marunouchi. 1993. Transforming growth factor-β suppresses activation and proliferation of microglia in vitro. J. Immunol. 151:2150.

31. Schluesener, H. J. 1990. Transforming growth factors type β1 and β2 suppress rat astrocyte autoantigen presentation and antagonize hyperinduction of class II major histocompatibility complex antigen expression by interferon-γ and tumor necrosis factor-α. J. Neuroimmunol. 27:41.

32. Lindholm, D., E. Castren, R. Kiefer, F. Zafra, and H. Thoenen. 1992. Transforming growth factor-β1 in the rat brain: increase after injury and inhibition of astrocyte proliferation. J. Cell Biol. 117:395.

33. Barnum, S. R. and J. L. Jones. 1994. Transforming growth factor-β1 inhibits inflammatory cytokine-induced C3 gene expression in astrocytes. J. Immunol. 152:765.

34. Karpus, W. J. and R. H. Swanborg. 1991. CD4[+] suppressor cells inhibit the function of effector cells of experimental autoimmune encephalomyelitis through a mechanism involving transforming growth factor-β1. J. Immunol. 146:1163.

35. Miller, A., O. Lider, A. B. Roberts, M. B. Sporn, and H. L. Weiner. 1992. Suppressor T cells generated by oral tolerization to myelin basic protein suppress both in vitro and in vivo immune responses by the release of transforming growth factor β after antigen-specific triggering. Proc. Natl. Acad. Sci. USA 89:421.

36. Stevens, D. B. and R. H. Swanborg. 1993. Cytokine-mediated regulation of tumor necrosis factor/lymphotoxin production by effector cells of autoimmune encephalomyelitis. J. Immunol. 150:246.

37. Johns, L. D., K. C. Flanders, G. E. Ranges, and S. Sriram. 1991. Successful treatment of experimental allergic encephalomyelitis with transforming growth factor-β1. J. Immunol. 147:1793.

38. Kuruvilla, A. P., R. Shah, G. M. Hochwald, H. D. Liggitt, M. A. Palladino, and G. J. Thorbecke. 1991. Protective effect of transforming growth factor β1 on experimental autoimmune diseases in mice. Proc. Natl. Acad. Sci. USA 88:2918.

39. Racke, M. K., S. D. Jalbut, B. Cannella, P. S. Albert, C. S. Raine, and D. E. McFarlin. 1991. Prevention and treatment of chronic relapsing experimental allergic encephalomyelitis by transforming growth factor-β1. J. Immunol. 146:3012.

40. Khoury, S. J., W. W. Hancock, and H. L. Weiner. 1992. Oral tolerance to myelin basic protein and natural recovery from experimental autoimmune encephalomyelitis are associated with downregulation of inflammatory cytokines and differential upregulation of transforming growth factor β, interleukin 4, and prostaglandin E expression in the brain. J. Exp. Med. 176:1355.

41. Santambrogio, L., G. M. Hochwald, B. Saxena, C.-H. Leu, J. E. Martz, J. A. Carlino, N. H. Ruddle, M. A. Palladino, L. I. Gold, and G. J. Thorbecke. 1993. Studies on the mechanisms by which transforming growth factor-β (TGF-β) protects against allergic encephalomyelitis: Antagonism between TGF-β and tumor necrosis factor. J. Immunol. 151:1115.

42. Nesbitt, J. E. and G. M. Fuller. 1992. Differential regulation of interleukin-6 receptor and gp130 gene expression in rat hepatocytes. Mol. Biol. of the Cell 3:103.

43. Bogdan, C., J. Paik, Y. Vodovotz, and C. Nathan. 1992. Contrasting mechanisms for suppression of macrophage cytokine release by transforming growth factor-β and interleukin-10. J. Biol. Chem. 267:23301.

44. Dubois, C. M., F. W. Ruscetti, E. W. Palaszynski, L. A. Falk, J. J. Oppenheim, and J. R. Keller. 1990. Transforming growth factor β is a potent inhibitor of interleukin 1 (IL-1) receptor expression: Proposed mechanism of inhibition of IL-1 action. J. Exp. Med. 172:737.

45. Pinson, D. M., R. D. LeClaire, R. B. Lorsbach, M. J. Parmely, and S. W. Russell. 1992. Regulation by transforming growth factor-β1 of expression and function of the receptor for IFN-γ on mouse macrophages. J. Immunol. 149:2028.

46. McGee, D. W., K. W. Beagley, W. K. Aicher, and J. R. McGhee. 1993. Transforming growth factor-β and IL-1β act in synergy to enhance IL-6 secretion by the intestinal epithelial cell line, IEC-6. J. Immunol. 151:970.

47. Elias, J. A., V. Lentz, and P. J. Cummings. 1991. Transforming growth factor-β regulation of IL-6 production by unstimulated and IL-1 stimulated human fibroblasts. J. Immunol. 146:3437.

48. Tanabe, O., S. Akira, T. Kamiya, G. G. Wong, T. Hirano, and T. Kishimoto. 1988. Genomic structure of the murine IL-6 gene: High degree of conservation of potential regulatory sequences between mouse and human. J. Immunol. 141:3875.

49. Isshiki, H., S. Akira, O. Tanabe, T. Nakajima, T. Shimamoto, T. Hirano, and T. Kishimoto. 1990. Constitutive and interleukin (IL-1)-inducible factors interact with the IL-1-responsive element in the IL-6 gene. Mol. Cell. Biol. 10:2757.

50. Akira, S., H. Isshiki, T. Nakajima, S. Kinoshita, Y. Nishio, S. Natsuka, and T. Kishimoto. 1992. Regulation of expression of the interleukin 6 gene: Structure and function of the transcription factor NF-IL6. Ciba Foundation Symposium 167:47.

51. Sparacio, S. M., Y. Zhang, J. Vilcek, and E. N. Benveniste. 1992. Cytokine regulation of interleukin-6 gene expression in astrocytes involves activation of an NF-κB-like nuclear protein. J. Neuroimmunol. 39:231.

52. Kim, S.-J., P. Angel, R. Lafyatis, K. Hattori, K. Y. Kim, M. B. Sporn, M. Karin, and A. B. Roberts. 1990. Autoinduction of transforming growth factor β1 is mediated by the AP-1 complex. Mol. Cell. Biol. 10:1492.

53. Rossi, P., G. Karsenty, A. B. Roberts, N. S. Roche, M. B. Sporn, and B. de Crombrugghe. 1988. A nuclear factor 1 binding site mediates the transcriptional activation of a type 1 collagen promoter by transforming growth factor-β. Cell 52:405.

54. Riccio, A., P. V. Pedone, L. R. Lund, T. Olesen, H. S. Olsen, and P. A. Andreasen. 1992. Transforming growth factor β1-responsive element: Closely associated binding sites for USF and CCAAT-binding transcription factor-nuclear factor I in the type 1 plasminogen activator inhibitor gene. Mol. Cell. Biol. 12:1846.

55. Lin, Y. A. and J. Stavnezer. 1992. Regulation of transcription of the germ-line Igα constant region gene by an ATF element and by novel transforming growth factor-β1-responsive elements. J. Immunol. 149:2914.

56. Loughlin, A. J., M. N. Woodroofe, and M. L. Cuzner. 1992. Regulation of Fc receptor and major histocompatibility complex antigen expression on isolated rat microglia by tumour necrosis factor, interleukin-1 and lipopolysaccharide: effect on interferon-gamma induced activation. Immunology 75:170.

57. Baker, D., J. K. O'Neill, and J. L. Turk. 1991. Cytokines in the central nervous system of mice during chronic relapsing experimental allergic encephalomyelitis. Cell. Immunol. 134:505.

58. Wahl, S. M., J. B. Allen, and N. M. Francis. 1991. Macrophage- and astrocyte-derived transforming growth factor β as a mediator of central nervous system dysfunction in acquired immune deficiency syndrome. J. Exp. Med. 173:981.

What is claimed is:

1. A method for modulating the expression of inflammatory cytokines in cells of the central nervous system, wherein said cells are not cells of the immune system, comprising administering an effective amount of TGF-β.

2. (Amended) A method for suppressing pro-inflammatory cytokines in cells of the central nervous system, wherein said cells are not cells of the immune system, comprising administering an effective amount of TGF-β.

3. A method for inducing anti-inflammatory cytokines in the central nervous system comprising administering an effective amount of TGF-β.

* * * * *